United States Patent
Inuzuka et al.

(10) Patent No.: US 12,372,518 B2
(45) Date of Patent: *Jul. 29, 2025

(54) METHOD FOR STABILIZING EXTRACELLULAR VESICLES

(71) Applicant: H.U. Group Research Institute G.K., Tokyo (JP)

(72) Inventors: Tatsutoshi Inuzuka, Tokyo (JP); Ayako Kurimoto, Tokyo (JP); Yuki Kawasaki, Tokyo (JP)

(73) Assignee: H.U. Group Research Institute G. K., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/544,491

(22) Filed: Dec. 19, 2023

(65) Prior Publication Data

US 2024/0118270 A1    Apr. 11, 2024

Related U.S. Application Data

(62) Division of application No. 16/955,553, filed as application No. PCT/JP2018/047098 on Dec. 20, 2018, now abandoned.

(30) Foreign Application Priority Data

Dec. 21, 2017 (JP) .................................. 2017-245603
Apr. 11, 2018 (JP) .................................. 2018-076185

(51) Int. Cl.
G01N 33/543 (2006.01)

(52) U.S. Cl.
CPC .............................. G01N 33/54306 (2013.01)

(58) Field of Classification Search
CPC ...... A61K 47/12; A61K 47/183; A61K 47/26; A61K 47/38; A61K 47/40; A61K 9/08; A61K 9/19; G01N 33/5076; G01N 33/54306; G01N 33/96
See application file for complete search history.

(56) References Cited

U.S. PATENT DOCUMENTS

| | | | |
|---|---|---|---|
| 11,614,388 B2 * | 3/2023 | Inuzuka | G01N 33/5076 424/450 |
| 2015/0125864 A1 | 5/2015 | Kang et al. | |
| 2019/0060367 A1 | 2/2019 | Zhang et al. | |
| 2019/0231694 A1 | 8/2019 | Lim | |
| 2019/0336539 A1 | 11/2019 | Wallace et al. | |
| 2019/0391163 A1 | 12/2019 | Stemmer et al. | |
| 2023/0194399 A1 * | 6/2023 | Inuzuka | G01N 33/68 424/450 |

FOREIGN PATENT DOCUMENTS

| | | | |
|---|---|---|---|
| WO | WO 2016/197196 A1 | | 12/2016 |
| WO | WO 2017/139795 | * | 8/2017 |
| WO | WO 2017/152035 A1 | | 9/2017 |
| WO | WO 2017/194499 A1 | | 11/2017 |
| WO | WO 2018/070939 A1 | | 4/2018 |

OTHER PUBLICATIONS

Kurimoto et al., "Enhanced recovery of CD9-positive extracellular vesicles from human specimens by chelating reagent," bioRxiv, 2020, Jun. 2020; pp. 1-15.*

Fuhrmann, G., et al. "Stability of extracellular vesicles during lyophilization-implication for their pharmaceutical use," Journal of Extracellular Vesicles, The 2nd United Kingdom Extracellular VesicleForum Meeting Abstracts, vol. 5, No. 1. Feb. 23, 2016, 2 pages.

International Search Report issued on Mar. 26, 2019 in PCT/JP2018/047098 filed on Dec. 20, 2018 citing documents AA, AO and AW therein, 1 page.

Extended European Search Report issued Oct. 26, 2021 in European Patent Application No. 18892197.7, citing documents AO through AQ and AX therein, 9 pages.

Bosch, S., et al., "Trehalose prevents aggregation of exosomes and cryodamage", Scientific Reports, vol. 6, No. 1, Nov. 8, 2016, XP055500173, pp. 1-11.

Aisen et al., "Effect of Trehalose and EDTA on Cryoprotective Action of Ram Semen Diluents", *Theriogenology*, 53:1053-1061 (2000).

* cited by examiner

*Primary Examiner* — Galina M. Yakovleva

(74) *Attorney, Agent, or Firm* — Oblon, McClelland, Maier & Neustadt, L.L.P.

(57) ABSTRACT

The present invention provides stabilization of an extracellular vesicle. Specifically, the present invention provides, for example, a method of stabilizing the extracellular vesicle including mixing an extracellular vesicle-containing sample with a saccharide and a chelating agent.

10 Claims, 10 Drawing Sheets

METHOD FOR STABILIZING EXTRACELLULAR VESICLES

CROSS REFERENCE TO RELATED APPLICATIONS

This application is a divisional of U.S. application Ser. No. 16/955,553 filed Jun. 18, 2020, pending, which is a National Stage of PCT/JP2018/047098 filed Dec. 20, 2018 and claims the benefit of JP 2017-245603 filed Dec. 21, 2017 and JP 2018-076185 filed Apr. 11, 2018.

TECHNICAL FIELD

The present invention relates to a method of stabilizing extracellular vesicle(s), and the like.

BACKGROUND ART

An extracellular vesicle is a microscopic vesicle secreted from various types of cells and having a membrane structure, and exists in body fluids such as blood. The extracellular vesicles secreted extracellularly include exosomes, ectosomes, and apoptotic blebs. Since the extracellular vesicle contains various substances that play a function such as intercellular signaling, it has been analyzed for the purposes of diagnosis, drug discovery and the like. Thus, it is required to develop a method of treating the extracellular vesicles useful for such analyses. For example, Patent Literature 1 describes: (1) capability of improving a yield of extracellular vesicles in the presence of EDTA (chelating agent) at a low concentration of approximately 3.0 mg/mL (approximately 10 µM) or less and incapability of improving the yield of extracellular vesicles in the presence of EDTA at a higher concentration (Example 1 and FIGS. 1A to 1C); (2) preserving extracellular vesicles in the presence of EDTA at low concentration of approximately 2.25 mg/ml (approximately 7.7 µM) at a certain temperature and time (Example 2, FIGS. 2A and 2B, 3A to 3F); and (3) freezing and thawing extracellular vesicles in the presence of EDTA at a low concentration of approximately 2.25 mg/ml (approximately 7.7 µM) (Example 3, FIGS. 4A and 4B).

PRIOR ART REFERENCES

Patent Literatures

Patent Literature 1: US Patent Application Publication No. 2015/0125864

SUMMARY OF INVENTION

Problem to Be Solved by the Invention

If extracellular vesicles can be stabilized, such extracellular vesicles are promising for improvement in preservability thereof and application to diagnosis, drug discovery and the like. Therefore, it is an object of the present invention to develop a method for stabilizing extracellular vesicle(s).

Solution to Problem

As a result of an extensive study, the inventors of the present invention have found that extracellular vesicle(s) in the extracellular vesicle-containing sample can be stabilized by mixing the extracellular vesicle-containing sample with a certain component such as a saccharide, and completed the present invention.

That is, the present invention is as follows.

[1] A method of stabilizing an extracellular vesicle, the method comprising mixing an extracellular vesicle-containing sample with a saccharide and a chelating agent.

[2] The method according to [1], wherein the extracellular vesicle is an exosome.

[3] The method according to [1] or [2], wherein the extracellular vesicle-containing sample is a body fluid or a culture supernatant.

[4] The method according to any of [1] to [3], wherein the extracellular vesicle-containing sample is a blood sample.

[5] The method according to any of [1] to [4], wherein a concentration of the saccharide in the mixing is 2.5 to 100 mg/mL.

[6] The method according to any of [1] to [5], wherein a concentration of the chelating agent in the mixing is 1 to 200 mM.

[7] A method of stabilizing an extracellular vesicle, the method comprising:
 (1) mixing an extracellular vesicle-containing sample with a saccharide; and
 (2) freezing a mixture of the extracellular vesicle-containing sample and the saccharide.

[8] The method according to [7], wherein the freezing is freeze-drying.

[9] A method of stabilizing an extracellular vesicle, the method comprising:
 (1) mixing an extracellular vesicle-containing sample with a chelating agent; and
 (2) freezing a mixture of the extracellular vesicle-containing sample and the chelating agent.

[10] The method according to [9], wherein the freezing is freeze-drying.

[11] An extracellular vesicle-stabilizing reagent comprising a saccharide and a chelating agent.

[12] An extracellular vesicle-cryopreservation stabilizing reagent comprising a saccharide or a chelating agent.

Effect of the Invention

The extracellular vesicle(s) can be stabilized in the extracellular vesicle-containing sample by mixing the extracellular vesicle-containing sample with the saccharide. Therefore, the present invention is useful, for example, in preservation of the extracellular vesicle(s).

EMBODIMENTS FOR CARRYING OUT THE INVENTION

1. Method of Stabilizing Extracellular Vesicle(s)

Figure 1:
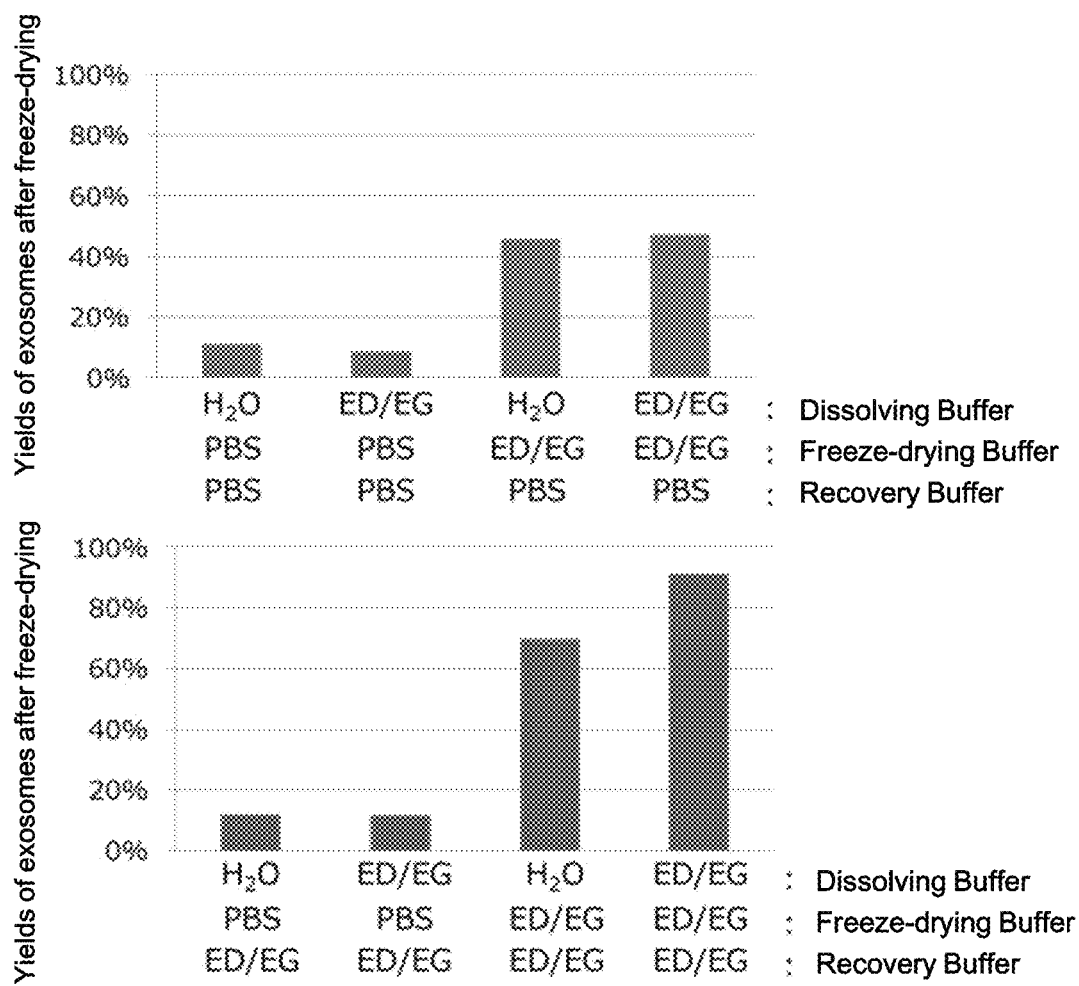
FIG. 1 includes graphs of yields of exosomes obtained after freeze-drying under various buffer conditions in Example 1. Yields of exosomes obtained without freeze-drying are defined as 100%.

The present invention provides a method of stabilizing an extracellular vesicle, including mixing an extracellular vesicle-containing sample with a saccharide.

The invention also provides the method of stabilizing the extracellular vesicle, including mixing the extracellular vesicle-containing sample with a chelating agent.

The invention also provides the method of stabilizing the extracellular vesicle, including mixing the extracellular vesicle-containing sample with the saccharide and the chelating agent.

The extracellular vesicle is a microscopic vesicle secreted from various types of cells and having a membrane structure. Examples of the extracellular vesicle include exosomes, ectosomes and apoptotic blebs. Preferably, the extracellular vesicle is the exosome. The extracellular vesicle can also be defined by its size. The size of the extracellular vesicle is, for example, 30 to 1000 nm, preferably 50 to 300 nm, and more preferably 80 to 200 nm. The size of the extracellular vesicle can be measured by, for example, a method based on Brownian movement of the extracellular vesicle, a light scattering method, and an electric resistance method, and the like. Preferably, the size of the extracellular vesicle is measured by NanoSight LM10 (manufactured by Malvern Instruments). In the case of using the NanoSight LM10, a measurement time of 30 seconds, three repetition times, and a detection threshold of 15 can be employed as measurement conditions. The extracellular vesicle can also be defined by using an extracellular vesicle marker. Examples of the extracellular vesicle marker include CD9, carcinoembryonic antigen (CEA), CD81, CD63, heat shock protein (HSP) 70, HSP90, major histocompatibility complex (MHC) I, tumor susceptibility gene (TSG) 101, lysosome associated membrane protein (LAMP) 1, intercellular adhesion molecule (ICAM)-1, integrin, ceramide, cholesterol, phosphatidylserine, ALIX, Annexins, Caveolin-I, Flotillin-I, Rab protein and EpCAM.

The extracellular vesicle-containing sample is any sample that contains the extracellular vesicle. Preferably, the extracellular vesicle-containing sample is a biological liquid sample. The extracellular vesicle-containing sample may be subjected to another treatment before being used for the method of the present invention. Examples of such a treatment include centrifugation, extraction, filtration, precipitation, heating, refrigeration, and stirring.

In one embodiment, the extracellular vesicle-containing sample is a culture supernatant. The culture supernatant may be a cell culture supernatant or a tissue culture supernatant. Examples of the organism from which a cell or a tissue to be cultured is derived include animals such as mammalian animals (e.g., primates such as humans and monkeys; rodents such as mice, rats and rabbits; farm animals such as cattle, pigs and goats; and working animals such as horses and sheep) and birds (e.g., chickens), insects, microorganisms (e.g., bacteria), plants and fish. Preferably, the organisms are mammalian animals such as humans.

In another embodiment, the extracellular vesicle-containing sample is a body fluid. The body fluid is derived from the organism as described above. Examples of the body fluid include blood samples (e.g., whole blood, serum and plasma), lymph fluid, tissue fluid, cerebrospinal fluid, ascites, saliva, pancreatic liquid, bile, sweat, seminal fluid, urine, tear fluid, mucosal fluid, breast fluid, thoracic fluid, bronchoalveolar lavage fluid and amnion fluid. Preferably, the body fluid is the blood.

In another embodiment, the extracellular vesicle-containing sample is a milk or a fruit juice.

The saccharide is a monosaccharide (e.g., aldose and ketose) or a polysaccharide in which two or more monosaccharides are linked by a glycosidic bond. In the present invention, the saccharides also include derivatives and saccharide alcohols. The derivative of the saccharide refers to a compound in which a hydrogen atom, a hydroxy group or a carbonyl group is substituted with a substituent in the saccharide. The saccharide alcohol refers to a compound in which the carbonyl group is reduced in the saccharide.

More specifically, examples of the monosaccharide include trioses (e.g., glyceraldehyde, dihydroxyacetone), tetroses (e.g., erythrose, threose, erythrose), pentoses (e.g., xylose, ribose, arabinose, lyxose, ribulose, xylulose, apiose), hexoses (e.g., glucose, fructose, galactose, mannose, allose, altrose, gulose, idose, talose, psicose, sorbose, tagatose), and heptoses (e.g., sedoheptulose, coriose). Examples of the aldose include xylose, glucose, galactose, mannose, glyceraldehyde, erythrose, threose, ribose, arabinose, lyxose, allose, altrose, gulose, idose, and talose. Examples of the ketose include fructose, dihydroxyacetone, erythrulose, xylulose, ribulose, psicose, sorbose, tagatose, sedoheptulose and coriose.

Examples of the polysaccharide include the polysaccharide in which two or more of the monosaccharides as described above are linked together. Preferably, examples of the polysaccharide include polysaccharides in which two or more monosaccharide units in one or plural kinds of are linked by a glycosidic bond (e.g., one or more glucose and one or more fructose are linked by a glycosidic bond), and the monosaccharide units are selected from the group consisting of glucose, fructose, galactose, mannose and xylose. Such a polysaccharide may be a linear polysaccharide or a cyclic polysaccharide. The linear polysaccharide may be a linear oligosaccharide or a linear polymer polysaccharide. In the case that the polysaccharide is the linear oligosaccharide, the total number of monosaccharide units in the polysaccharide may be, for example, 2 to 20, preferably 2 to 10, more preferably 2 to 6, and still more preferably 2 to 4. For example, in the case that the polysaccharide is a polysaccharide in which one or more glucose and one or more fructose are linked by a glycosidic bond, each of the numbers of glucose and fructose in the polysaccharide may be, for example, 1 to 10, preferably 1 to 5, more preferably 1 to 3, and still more preferably 1 or 2. The linear oligosaccharide may be a disaccharide, for example. Examples of the disaccharide include sucrose, lactose, and trehalose. Particularly preferably, the disaccharide is sucrose in which one glucose and one fructose are linked by a glycosidic bond. Examples of the linear polymer polysaccharide include cellulose, amylose, amylopectin, glucomannan, pullulan, galactomannan, inulin, glycogen, chitin, chitosan, glucuronoxylan, arabinoxylan, agarose, carrageenan, pectin, pectinic acid, alginic acid, fucoidan, chondroitin sulfate and hyaluronan. In the case that the polysaccharide is the cyclic polysaccharide, the total number of monosaccharide units in the polysaccharide may be, for example, 5 to 100, preferably 5 to 20, more preferably 5 to 10, and still more preferably 6 to 8. Examples of the cyclic polysaccharide include cyclodextrins (α-cyclodextrin, (β-cyclodextrin and γ-cyclodextrin).

Examples of the substituent in the saccharide derivative include a hydrogen atom, a hydroxy group, a $C_{1-6}$ alkyl group, a $C_{1-6}$ alkenyl group, a $C_{1-6}$ alkynyl group, a $C_{1-6}$ alkyloxy (alkoxy) group, a $C_{6-14}$ aromatic hydrocarbon group, a $C_{1-6}$ alkyl-carbonyl (acyl) group, a carboxy group, a nitro group, an amino group and a cyano group.

The $C_{1-6}$ alkyl group is an alkyl having one to six carbon atom(s), and may be linear, branched or cyclic, and the linear or branched alkyl is preferable. Examples of the $C_{1-6}$ alkyl group include methyl, ethyl, propyl, iso-propyl, butyl, iso-butyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl. The $C_{1-6}$ alkyl group is preferably a $C_{1-4}$ alkyl group, and more preferably a $C_{1-3}$ alkyl group.

The $C_{1-6}$ alkenyl group is an alkenyl group having one to six carbon atom(s), and may be linear, branched or cyclic, and the linear or branched alkenyl is preferable. Examples of the $C_{1-6}$ alkenyl group include ethenyl (vinyl), propenyl, butenyl, pentenyl and hexenyl. The $C_{1-6}$ alkenyl group is preferably a $C_{1-4}$ alkenyl group, and more preferably a $C_{1-3}$ alkenyl group.

The $C_{1-6}$ alkynyl group is an alkynyl group having one to six carbon atom(s), and may be linear, branched or cyclic, and the linear or branched alkynyl is preferable. Examples of the $C_{1-6}$ alkynyl group include ethynyl, propynyl, butynyl, pentynyl and hexynyl. The $C_{1-6}$ alkynyl group is preferably a $C_{1-4}$ alkynyl group, and more preferably a $C_{1-3}$ alkynyl group.

The $C_{1-6}$ alkyloxy group is an alkyloxy group having one to six carbon atom(s). Examples of the $C_{1-6}$ alkyloxy group include methyloxy, ethyloxy, propyloxy, iso-propyloxy, butyloxy, iso-butyloxy, sec-butyloxy, tert-butyloxy, pentyloxy, isopentyloxy, neopentyloxy, 1-ethylpropyloxy, hexyloxy, isohexyloxy, 1,1-dimethylbutyloxy, 2,2-dimethylbutyloxy, 3,3-dimethylbutyloxy and 2-ethylbutyloxy. The $C_{1-6}$ alkyloxy group is preferably a $C_{1-4}$ alkyloxy group, and more preferably a $C_{1-3}$ alkyloxy group.

Examples of the $C_{6-14}$ aromatic hydrocarbon group include phenyl, naphthyl, and anthracenyl. The $C_{6-14}$ aromatic hydrocarbon group is preferably phenyl or naphthyl, and more preferably phenyl.

The $C_{1-6}$ alkyl-carbonyl (acyl) group is a carbonyl group having the $C_{1-6}$ alkyl group as described above. Examples of the $C_{1-6}$ alkyl-carbonyl group include methylcarbonyl (acetyl), ethylcarbonyl, propylcarbonyl, iso-propylcarbonyl, butylcarbonyl, iso-butylcarbonyl, sec-butylcarbonyl, tert-butylcarbonyl, pentylcarbonyl, isopentylcarbonyl, neopentylcarbonyl, 1-ethylpropylcarbonyl, hexylcarbonyl, isohexylcarbonyl, 1,1-dimethylbutylcarbonyl, 2,2-dimethylbutylcarbonyl, 3,3-dimethylbutylcarbonyl and 2-ethylbutylcarbonyl. The $C_{1-6}$ alkylcarbonyl group is preferably a $C_{1-4}$ alkylcarbonyl group, and more preferably a $C_{1-3}$ alkylcarbonyl group.

These substituents may be further substituted with other substituents. Examples of the other substituents include hydroxy groups, carboxy groups, nitro groups, amino groups and cyano groups.

Examples of the derivative of saccharide substituted with the substituent include cyclic polysaccharides (e.g., cyclodextrin such as α-cyclodextrin, β-cyclodextrin, γ-cyclodextrin and the like), and derivatives of the linear polymer polysaccharide (e.g., cellulose). Examples of the derivative of the cyclic polysaccharide include cyclic polysaccharides substituted with a substitutable alkyl group (e.g., methyl-β-cyclodextrin and hydroxypropyl-β-cyclodextrin). Examples of the derivative of the linear polymer polysaccharide includes a cellulose derivative.

The cellulose derivative is a cellulose derivative in which a hydrogen atom of at least one hydroxy group of the cellulose is substituted with a hydrophilic group. Examples of the hydrophilic group in the cellulose derivative include carboxyalkyl (e.g., carboxy $C_{1-6}$ alkyl) and hydroxyalkyl (e.g., hydroxy $C_{1-6}$ alkyl). The hydrophilic group in the cellulose derivative is preferably carboxyalkyl or hydroxyalkyl.

Examples of the carboxyalkyl include carboxymethyl, carboxyethyl (1-carboxyethyl and 2-carboxyethyl), carboxypropyl (1-carboxypropyl, 2-carboxypropyl and 3-carboxypropyl), carboxyisopropyl (1-carboxy-2-methylethyl) and 2-carboxy-2-methylethyl), carboxybutyl (1-carboxybutyl, 2-carboxybutyl, 3-carboxybutyl and 4-carboxybutyl), carboxy t-butyl, carboxypentyl (1-carboxypentyl, 2-carboxypentyl, 3-carboxypentyl, 4-carboxypentyl and 5-carboxypentyl), carboxyhexyl (1-carboxyhexyl, 2-carboxyhexyl, 3-carboxyhexyl, 4-carboxyhexyl, 5-carboxyhexyl and 6-carboxyhexyl).

Examples of the hydroxyalkyl include hydroxymethyl, hydroxyethyl (1-hydroxyethyl and 2-hydroxyethyl), hydroxypropyl (1-hydroxypropyl, 2-hydroxypropyl and 3-hydroxypropyl), hydroxyisopropyl (1-hydroxy-2-methylethyl and 2-hydroxy-2-methylethyl), hydroxybutyl (1-hydroxybutyl, 2-hydroxybutyl, 3-hydroxybutyl and 4-hydroxybutyl), hydroxy t-butyl, hydroxypentyl (1-hydroxypentyl, 2-hydroxypentyl, 3-hydroxypentyl, 4-hydroxypentyl and 5-hydroxypentyl) and hydroxyhexyl (1-hydroxyhexyl, 2-hydroxyhexyl, 3-hydroxyhexyl, 4-hydroxyhexyl, 5-hydroxyhexyl and 6-hydroxyhexyl).

Specific examples of the cellulose derivative include carboxymethyl cellulose, hydroxyethyl cellulose, hydroxypropyl cellulose or hydroxypropylmethyl cellulose.

The cellulose derivative also includes a nanocellulose derivative. The nanocellulose derivative is a derivative of the nanocellulose described below.

The nanocellulose is a fibrous cellulose having a fiber width in a nanometer order. The fiber width of the nanocellulose is, for example, 500 nm or less, and may be preferably 200 nm or less, more preferably 100 nm or less, still more preferably 50 nm or less, still further more preferably 10 nm or less, and particularly preferably 5 nm or less.

Examples of the cellulose derivatives also include salts thereof. Examples of the salt includes salts of metal (e.g., a monovalent metal such as lithium, sodium, potassium, rubidium and cesium; and a bivalent metal such as calcium, magnesium and zinc), and salts of inorganic base (e.g., ammonia).

Examples of the saccharide alcohol include: the monomer in which the carbonyl group is reduced in the monosaccharide as described above; a multimer in which the monomers are linked together, for example, by glycosidic bonds; and a multimer in which the monomer and the monosaccharide as constituent units are linked together, for example, by glycosidic bonds. Examples of the monomer include tritols (e.g., glycerin), tetritols (e.g., erythritol and threitol), pentitols (e.g., xylitol, arabinitol and ribitol), hexitols (e.g., sorbitol, mannitol, iditol and galactitol), heptitols (e.g., volemitol and perseitol), and octyltols (e.g., erythrogalactooctytol). Examples of the saccharide alcohol include: monomers such as xylitol, sorbitol, mannitol, galactitol, fucitol, volemitol, arabinitol, glycerin, iditol, erythritol, threitol, ribitol and the like; and dimers such as lactitol and maltitol.

In the present invention, a mixture of two or more (e.g., two, three, four and five) kinds of saccharides may be mixed with the extracellular vesicle-containing sample. The present invention may include adding the saccharide to the extracellular vesicle-containing sample before mixing the extracellular vesicle-containing sample with the saccharide. The saccharide may be added simultaneously with or separately from the chelating agent.

In the case of mixing the extracellular vesicle-containing sample with the saccharide, the concentration of the saccharide in the mixing is not particularly limited as long as the extracellular vesicle(s) can be stabilized. Such a concentration varies depending on factors such as kinds of the saccharides, and may be, for example, 2.5 mg/ml or more, preferably 3.0 mg/mL or more, more preferably 3.5 mg/mL or more, still more preferably 4.0 mg/mL or more, still further more preferably 4.5 mg/mL or more, and particularly preferably 5.0 mg/mL or more, 6.0 mg/mL or more, 8.0 mg/mL or more or 10.0 mg/mL or more. Also, such a concentration varies depending on factors such as the kinds of saccharides, and may be, for example, 600 mg/mL or less, 400 mg/mL or less, 200 mg/mL or less, or 100 mg/mL or less, and may be preferably 95 mg/mL or less, more preferably 90 mg/mL or less, still more preferably 85 mg/mL or less, still further more preferably 80 mg/mL or less, and particularly preferably 75 mg/mL or less, 70 mg/mL or less, 60 mg/mL or less, or 50 mg/mL or less. More specifically, the concentration of the saccharide varies depending on factors such as the kinds of saccharides, and may be, for example, 2.5 to 800 mg/mL, 2.5 to 600 mg/mL, 2.5 to 400 mg/mL, 2.5 to 200 mg/mL or 2.5 to 100 mg/mL, and may be preferably 3.0 to 95 mg/mL, more preferably 3.5 to 90 mg/mL, still more preferably 4.0 to 85 mg/mL, still further more preferably 4.5 to 80 mg/mL, and particularly preferably 5.0 to 75 mg/mL, 6.0 to 70 mg/mL, 8.0 to 60 mg/mL or 10.0 to 50 mg/mL.

The chelating agent is a compound having a coordination moiety capable of coordinating with a metal ion, or a salt thereof. The number of the coordination moiety(ies) is preferably 2 or more, more preferably 3 or more (e.g., 3 or 6). Examples of the coordination atom as the coordination moiety include an oxygen atom, a phosphorus atom, a nitrogen atom, a sulfur atom and a chlorine atom. The coordination atom is preferably the oxygen atom or the phosphorus atom, and more preferably the oxygen atom. Examples of a coordination group as the coordination moiety include a group having the abovementioned coordination atom. The coordination group is preferably a carboxylic acid group or a phosphoric acid group, and more preferably the carboxylic acid group.

Examples of the chelating agent include ethylenediaminetetraacetic acid (EDTA), glycoletherdiaminetetraacetic acid (EGTA), hydroxyethyl ethylenediaminetriacetic acid (HEDTA), hydroxyethyl iminodiacetic acid (HIDA), nitrilotriacetic acid (NTA), oxalic acid, ethylenediaminetetra(methylene phosphoric acid) (EDTMP) and salts thereof. Examples of the salts include metal salts (e.g., monovalent metal salts such as sodium salts, potassium salts, and bivalent metal salts such as calcium salts, magnesium salts), inorganic salts (e.g., halide salts such as fluoride, chloride, bromide and iodide, and ammonium salts), organic salts (e.g., ammonium salts substituted with an alkyl group), and acid addition salts (e.g., salts with an inorganic acid such as sulfuric acid, hydrochloric acid, hydrobromic acid, nitric acid, phosphoric acid and the like, and salts with an organic acid such as acetic acid, oxalic acid, lactic acid, citric acid, trifluoromethanesulfonic acid, trifluoroacetic acid and the like). In the present invention, a mixture of 2 or more (e.g., 2, 3, 4, or 5) kinds of chelating agents may be mixed with the extracellular vesicle-containing sample. The present invention may include adding the chelating agent to the extracellular vesicle-containing sample before mixing the extracellular vesicle-containing sample with the chelating agent.

In the case of mixing the extracellular vesicle-containing sample with the chelating agent, a concentration of the chelating agent in the mixing is not particularly limited as long as the extracellular vesicle(s) can be stabilized. Such a concentration varies depending on factors such as kinds of the chelating agents, and may be, for example, 1 mM or more, preferably 5 mM or more, more preferably 10 mM or more, still more preferably 15 mM or more, still further more preferably 20 mM or more, and particularly preferably 30 mM or more, 40 mM or more, or 50 mM or more. Also, such a concentration varies depending on factors such as the kinds of chelating agents, and may be, for example, 200 mM or less, preferably 180 mM or less, more preferably 170 mM or less, still more preferably 160 mM or less, still further more preferably 150 mM or less, and particularly preferably 140 mM or less, 120 mM or less, or 100 mM or less. More specifically, the concentration of the chelating agent may be, for example, 1 mM to 200 mM, preferably 5 to 180 mM, more preferably 10 to 170 mM, still more preferably 15 to 160 mM, still further more preferably 20 to 150 mM, and particularly preferably 30 to 140 mM, 40 to 120 mM, or 50 to 100 mM.

The extracellular vesicle-containing sample may be mixed with both of the saccharide and the chelating agent.

In the case of using both the saccharide and the chelating agent in the present invention, concentrations of the saccharide and the chelating agent to be used in the mixing can also be defined by their ratio. For example, the concentration of the chelating agent per 10 mg/mL of the saccharide in the mixing varies depending on factors such as the kinds of saccharide and chelating agent, and may be, for example, 1 mM or more, preferably 5 mM or more, preferably 10 mM or more, still more preferably 15 mM or more, still further more preferably 20 mM or more, and particularly preferably 30 mM or more, 40 mM or more, or 50 mM or more. Also, such a concentration varies depending on factors such as the kinds of saccharide and chelating agent, and may be, for example, 200 mM or less, preferably 180 mM or less, more preferably 170 mM or less, still more preferably 160 mM or less, still further more preferably 150 mM or less, and particularly preferably 140 mM or less, 120 mM or less, or 100 mM or less. More specifically, the concentration of the chelating agent may be, for example, 1 mM to 200 mM, preferably 5 to 180 mM, more preferably 10 to 170 mM, still more preferably 15 to 160 mM, still further more preferably 20 to 150 mM, and particularly preferably 30 to 140 mM, 40 to 120 mM, or 50 to 100 mM.

The mixing can be carried out in any way. For example, in the case of using both the saccharide and the chelating agent in the present invention, the mixing can be carried out simultaneously or separately. More specifically, the extracellular vesicle-containing sample may be (1) mixed with the saccharide and the chelating agent simultaneously, (2) mixed with the chelating agent after being mixed with the saccharide, or (3) mixed with the saccharide after being mixed with the chelating agent. From the viewpoint of convenience in processing and so on, preferably, the extracellular vesicle-containing sample may be mixed with the saccharide and the chelating agent simultaneously.

A mixing temperature may be, for example, 4 to 37° C., and preferably 15 to 30° C. A mixing time is not particularly limited as long as the extracellular vesicle(s) can be stabilized, and can be controlled as appropriate. The extracellular vesicle-containing sample may be left to stand after being mixed with a certain component such as the saccharide.

Whether the extracellular vesicle is stabilized by the mixing with the certain component such as the saccharide can be assessed, for example, by: comparing an index value that is measured after the mixing the extracellular vesicle with the certain component such as the saccharide, with a control value measured (under the same condition other than the presence or absence of the certain component such as the saccharide) for the extracellular vesicle in absence of the certain component such as the saccharide; and determining whether the index value is superior to the control value. For example, stability of a freeze-dried product may be assessed by: freeze-drying with a freeze dryer (manufactured by Tokyo Rikakikai Co., Ltd.) by setting a program at −28° C. for 2 hours, at −10° C. for 4 hours and at 20° C. subsequently; and comparing the index values of the freeze-dried products in the presence and absence of the certain component such as the saccharide. For example, as such an index value, it is possible to utilize an amount of an extracellular vesicle-marker and a measurement value of the number of particles corresponding to the extracellular vesicle.

The amount of the extracellular vesicle-marker can be measured by any well-known method in the relevant field.

In the case that the extracellular vesicle-marker is a protein, examples of the measurement method include immunoassay and mass spectrometry. Examples of the immunoassay include a direct competitive method, an indirect competitive method and a sandwich method. Also, examples of such an immunoassay include chemiluminescent immunoassay (CLIA) [e.g., a chemiluminescent enzyme immunoassay (CLEIA)], turbidimetric immunoassay (TIA), enzyme immunoassay (EIA) (e.g., direct competitive ELISA, indirect competitive ELISA, and sandwich ELISA), radioimmunoassay (RIA), latex agglutination reaction method, fluorescence immunoassay (FIA), and immunochromatography, Western blotting, immunostaining and fluorescence activated cell sorting (FACS). In the case of detecting multiple components, proteomic analysis may be performed.

In the case that the extracellular vesicle-marker is a nucleic acid, examples of the measurement method include a hybridization method using a probe, a gene amplification method using a primer(s) (e.g., 2, 3 or 4 primers) and mass spectrometry.

In the case that the extracellular vesicle-marker is a component other than the protein and the nucleic acid, examples of the measurement method include immunoassays and mass spectrometric method. In the case of detecting multiple components, metabolome analysis may be performed.

The number of particles corresponding to the extracellular vesicle(s) can be measured, for example, with an instrument such as a particle analysis instrument, an electron microscope, a flow cytometer and the like. Preferably, such a measurement of particle counts can be performed by NanoSight LM10 (manufactured by Malvern Instruments Ltd.). In the case of using NanoSight LM10, it is possible to employ measurement conditions of 30 seconds measurement time, three repeating times and a detection threshold of 15.

The method of the present invention may further include freezing the mixture.

That is, the present invention further provides the method of stabilizing the extracellular vesicle. The method further includes:
 (1) mixing the extracellular vesicle-containing sample with the saccharide; and
 (2) freezing the mixture of the extracellular vesicle-containing sample and the saccharide.

The present invention further provides the method of stabilizing the extracellular vesicle. The method further includes:
 (1) mixing the extracellular vesicle-containing sample with the chelating agent; and
 (2) freezing the mixture of the extracellular vesicle-containing sample and the chelating agent.

The present invention further provides the method of stabilizing the extracellular vesicle. The method further includes:
 (1) mixing the extracellular vesicle-containing sample with the saccharide and the chelating agent; and
 (2) freezing the mixture of the extracellular vesicle-containing sample, the saccharide and the chelating agent.

The freezing may be either the freeze-drying or a freezing of solution (non-freeze-drying). The freeze-drying is preferred in the case of preserving the extracellular vesicle(s) for a longer period.

The examples are described above, as to the kinds of the saccharide and the chelating agent as well as their concentrations in the mixing.

2. Extracellular Vesicle-Stabilizing Reagent

The present invention also provides an extracellular vesicle-stabilizing reagent. The reagent of the present invention contains the saccharide or the chelating agent. Preferably, the reagents of the present invention may contain the saccharide and the chelating agent. The saccharide and the chelating agent are the same as those described above. The reagent of the present invention may include another component (e.g., another component useful in the stabilization of extracellular vesicle(s)), in addition to the saccharide and chelating agents.

In one embodiment, the reagent of the present invention is an extracellular vesicle-stabilizing composition containing the saccharide. In another embodiment, the reagent of the present invention is an extracellular vesicle-stabilizing composition containing a chelating agent. In yet another embodiment, the composition of the present invention is an extracellular vesicle-stabilizing composition containing both the saccharide and the chelating agent.

In order to stabilize the extracellular vesicle(s), the reagent of the present invention can be mixed with the extracellular vesicle-containing sample for use. For the purpose of preserving the extracellular vesicle(s) stably, the mixture of the extracellular vesicle-containing sample and the reagent of the present invention may be frozen. In this case, the reagent of the present invention can be used as an extracellular vesicle-cryopreservation stabilizing reagent. The freezing can be either the freeze-drying or the freezing of solution (non-freeze-drying). The freeze-drying is preferred in the case of preserving the extracellular vesicle(s) for a longer period.

The concentration of the saccharide in the composition is not particularly limited, as long as the extracellular vesicle(s) can be stabilized after the mixing with the extracellular vesicle-containing sample. Such a concentration varies depending on factors such as the kind of the saccharide, and may be, for example, 2.7 mg/mL or more, preferably 3.0 mg/mL or more, more preferably 3.5 mg/mL or more, still more preferably 4.0 mg/mL or more, still further more preferably 4.5 mg/mL or more, and particularly preferably 5.0 mg/mL or more, 6.0 mg/mL or more, 8.0 mg/mL or more, or 10.0 mg/mL or more. Also, such a concentration varies depending on factors such as the kind of saccharide, and may be, for example, 600 mg/mL or less, 400 mg/mL or less, 200 mg/mL or less, or 100 mg/mL or less, preferably 95 mg/mL or less, more preferably 90 mg/mL or less, still more preferably 85 mg/mL or less, still further more preferably 80 mg/mL, particularly preferably 75 mg/mL or less, 70 mg/mL or less, 60 mg/mL or less, or 50 mg/mL or less. More specifically, the concentration of the saccharide varies depending on factors such as the kind of saccharide, and may be, for example, 2.7 to 800 mg/mL, 2.7 to 600 mg/mL, 2.7 to 400 mg/mL, 2.7 to 200 mg/mL or 2.7 to 100 mg/mL, preferably 3.0 to 95 mg/mL, more preferably 3.5 to 90 mg/mL, still more preferably 4.0 to 85 mg/mL, still further more preferably 4.5 to 80 mg/mL, and particularly preferably 5.0 to 75 mg/mL, 6.0 to 70 mg/mL, 8.0 to 60 mg/mL or 10.0 to 50 mg/mL.

The concentration of the chelating agent in the composition is not particularly limited, as long as the extracellular vesicle(s) can be stabilized after the mixing with the extracellular vesicle-containing sample. Such a concentration varies depending on factors such as the kind of the chelating agent, and may be, for example, 1.1 mM or more, preferably 5 mM or more, preferably 10 mM or more, preferably 15 mM or more, more preferably 20 mM or more, still more preferably 30 mM or more, still further more preferably 40 mM or more, and particularly preferably 50 mM or more. Also, such a concentration varies depending on factors such as the kind of chelating agents, and may be, for example, 200 mM or less, preferably 180 mM or less, more preferably 170 mM or less, still more preferably 160 mM or less, still further more preferably 150 mM or less, and particularly preferably 140 mM or less, 120 mM or less, or 100 mM or less. More specifically, the concentration of the chelating agent may be, for example, 1.1 mM to 200 mM, preferably 5 to 180 mM, more preferably 10 to 170 mM, still more preferably 15 to 160 mM, still further more preferably 20 to 150 mM, and particularly preferably 30 to 140 mM, 40 to 120 mM, or 50 to 100 mM.

In the case that the composition of the present invention contains both the saccharide and the chelating agent, the concentrations of the saccharide and the chelating agent can also be defined by their ratio. For example, the concentration of the chelating agent per 10 mg/mL of the saccharide varies depending on factors such as the kinds of saccharide and chelating agent, and may be, for example, 1 mM or more, preferably 5 mM or more, preferably 10 mM or more, preferably 15 mM or more, more preferably 20 mM or more, still more preferably 30 mM or more, still further more preferably 40 mM or more, and particularly preferably 50 mM or more. Also, such a concentration varies depending on factors such as the kinds of saccharide and chelating agents, and may be, for example, 200 mM or less, preferably 180 mM or less, more preferably 170 mM or less, still more preferably 160 mM or less, still further more preferably 150 mM or less, and particularly preferably 140 mM or less, 120 mM or less, or 100 mM or less. More specifically, the concentration of the chelating agent may be, for example, 1 mM to 200 mM, preferably 5 to 180 mM, more preferably 10 to 170 mM, still more preferably 15 to 160 mM, still further more preferably 20 to 150 mM, and particularly preferably 30 to 140 mM, 40 to 120 mM, or 50 to 100 mM.

The composition of the present invention is dissolved in an aqueous solution for use. The composition of the present invention may be either a non-aqueous composition (e.g., mixture powder) containing the saccharide and/or the chelating agent or an aqueous solution containing the saccharide and/or the chelating agent. From the viewpoint of quick and simple use and so on, the aqueous solution containing the saccharide and/or the chelating agent is preferred. Examples of the aqueous solution include water (e.g., distilled water, sterilized water, sterilized distilled water and pure water) and buffer. The buffer is preferred. Examples of the buffer include phosphate buffer, phosphate-buffered saline (PBS), tartrate buffer, citrate buffer, acetate buffer, glycine buffer, carbonate buffer, 2-morpholinoethanesulfonic acid (MES) buffer, tris(hydroxymethyl)aminomethane (Tris) buffer, borate buffer, 3-morpholinoproponesulfonic acid (MOPS) buffer, N,N-bis(2-hydroxyethyl)glycine (Bicine) buffer, N,N-bis(2-hydroxyethyl)glycine (Bis-Tris) buffer and 2-[4-(2-hydroxyethyl)1-piperazinylethanesulfonic acid (HEPES) buffer. It is preferable that the buffer has neutral pH. More specifically, such a pH is preferably 5.0 or more, more preferably 5.5 or more, and still more preferably 6.0 or more. Also, the pH is preferably 9.0 or less, more preferably 8.5 or less, and still more preferably 8.0 or less. The pH can be measured by well-known methods in the relevant field. Preferably, it is possible to employ a value measured at 25° C. with a pH meter having a glass electrode, as the pH.

The composition of the present invention can be used by being mixed with the extracellular vesicle-containing sample as appropriate. A mixing ratio of the composition of the present invention and the extracellular vesicle-containing sample (the extracellular vesicle-containing sample/the composition) is, for example, 1/30 to 30, preferably 1/20 to 20, more preferably 1/10 to 10, and still more preferably 1/10 to 1.

In the case that the composition of the present invention is the aqueous solution, a volume of the aqueous solution is, for example, 1 μL to 100 mL. Preferably, the volume of the aqueous solution may be 10 μL or more, 100 μL or more, or 1000 μL or more. Also, the volume of the aqueous solution may be 50 mL or less, 10 mL or less, or 2 mL or less.

In another embodiment, the reagent of the present invention is a kit including the saccharide and/or the chelating agent. The saccharide and/or the chelating agent can be provided in a solid form or in an aqueous solution form, and is preferably provided in the aqueous solution form. Therefore, the kit of the present invention may be provided in an aqueous solution form containing the saccharide, may be provided in an aqueous solution form containing the chelating agent, may be provided in an aqueous solution form containing both the saccharide and the chelating agent, or may be provided in a first aqueous solution form containing the saccharide and a second aqueous solution form containing the chelating agent. The aqueous solution is described above, and preferably the buffer. Examples and pH of the buffer are described above. The abovementioned concentrations of saccharide and chelating agent in the composition of the present invention can be applied also to a concentration of the saccharide in the first aqueous solution, a concentration of the chelating agent in the second aqueous solution and a concentration ratio of the saccharide in the first aqueous solution and the chelating agent in the second aqueous solution. The abovementioned mixing ratios and the volumes in the composition of the present invention can be applied also to a mixing ratio of the first and second aqueous solutions and the extracellular vesicle-containing sample and volumes of the first and second aqueous solutions.

3. Mixture Containing Extracellular Vesicle(s)

The present invention also provides a mixture containing the saccharide and/or the chelating agent, and the extracellular vesicle. The mixture of the present invention may further include the aqueous solution (e.g., the buffer solution described above). The form of the mixture is not particularly limited, and preferably the aqueous solution or a frozen product thereof (e.g., a freeze-dried product). The mixture of the present invention can be obtained by treating the extracellular vesicle-containing sample in the method of the present invention or with the reagent thereof as described above. For example, the mixture of the present invention is useful in preservation of the extracellular vesicle(s).

The concentrations described above regarding the method of the present invention can be applied also to a concentration of the saccharide or the chelating agent in the mixture, and a concentration ratio of the saccharide and the chelating agent. The concentration (particle counts/mL) of extracellular vesicle(s) in the mixture is, for example, $1\times10^2$ to $1\times10^{15}$, preferably $1\times10^3$ to $1\times10^{14}$, more preferably $1\times10^4$ to $1\times10^{13}$, still more preferably $1\times10^5$ to $1\times10^{12}$, and particularly preferably $1\times10^6$ to $1\times10^{11}$.

In the case that the mixture of the present invention is the aqueous solution, volume of the aqueous solution is, for example, 1 μL to 100 mL. Preferably, the volume of aqueous solution may be 10 μL or more, 100 μL or more, or 1000 μL or more. Also, the volume of aqueous solution may be 50 mL or less, 10 mL or less, or 2 mL or less.

EXAMPLES

Hereinafter, the present invention will be described with reference to Examples, but the present invention is not limited to these Examples.

Example 1: Stabilization of Exosome with Chelating Agent

The influence of chelating agent on freeze-drying of exosomes was investigated.
1) Recovery of Exosomes A culture supernatant of human non-small cell lung carcinoma cell line H1299 cultured in serum-free medium for three days was used as a sample. The culture supernatant was centrifuged at 2,000×g at 4° C. for 5 minutes, then filtered through a 0.22 μm filter (manufactured by Millipore Corp.), and then concentrated using Amicon Ultra-15 (manufactured by Millipore Corp.). The concentrate was centrifuged at 20,000×g at 4° C. for 15 minutes. Then, the supernatant was centrifuged at 100,000×g at 4° C. for 1 hour. The supernatant was discarded, and then PBS (2.9 mM $NaH_2PO_4$, 9.0 mM $Na_2HPO_4$, 137 mM NaCl) or 50 mM EDTA/50 mM EGTA/PBS was added to resuspend the precipitate. Then, the resuspension was centrifuged at 100,000×g at 4° C. for 1 hour. The supernatant was discarded, and PBS or 50 mM EDTA/50 mM EGTA/PBS (recovery buffer) was newly added to resuspend the precipitate in order to recover exosomes.
2) Freeze-Drying of Exosomes Protein quantification was performed for the recovered exosomes with Qubit (trademark) Protein Assay Kit (manufactured by Thermo Fisher Scientific Inc.). Then, the recovery buffer was further added to each of the recovered exosomes so as to prepare solutions containing the same concentration of protein. Next, 1 volume of the recovered exosomes was mixed with 24 volumes of the freeze-drying buffer. After dispensation, the solution was freeze-dried with a freeze dryer (manufactured by Tokyo Rikakikai Co., Ltd.) with a program of −28° C. for 2 hours, −10° C. for 4 hours and subsequent 20° C., in order to obtain a freeze-dried product containing freeze-dried exosomes. As the freeze-drying buffer, PBS or EDTA/EGTA/PBS (final conc. 50 mM EDTA/50 mM EGTA) was used. pH of PBS used was 7.4 (same in Examples 1 to 3).

Subsequently, the freeze-dried product was dissolved in milli-Q water (manufactured by Millipore Corp.) or 50 mM EDTA/50 mM EGTA/$H_2O$ (dissolving buffer).
3) Assessment of Stability of Exosomes Based on Measurement of Amount of Exosome-Specific Antigen (CD9)

The amount of the dissolved freeze-dried exosomes was measured by ELISA system. Specifically, PBS (pH 7.4) containing anti-CD9 antibody prepared in the applicant was added to a 96-well ELISA plate (manufactured by NUNC Inc.), and incubated overnight at 4° C. Then, each well was washed three times with PBS containing 0.05 wt % of Tween (registered trademark) 20 (PBS-T), 200 μL of PBS containing 0.5 wt % Casein was added, and incubated for 2 hours at room temperature. After washing with PBS-T, 100 μL of the dissolved freeze-dried product diluted with PBS was added to each well and incubated for 1 hour at 37° C. Then, after washing with PBS-T, 100 μL of PBS containing biotinylated anti-CD9 antibody prepared in the applicant and streptavidin conjugated alkaline phosphatase (SA-ALP, manufactured by GeneTex Co.) was added to each well, and then incubated for 1 hour at 37° C. Then, after washing with PBS, 100 μL of Lumipulse (registered trademark) substrate solution (manufactured by Fujirebio Inc.) was added to be allowed to react for 10 minutes at 37° C., and then emission count was measured at a 477 nm wavelength. The count of the sample obtained without freeze-drying is defined as 100%.

As a result, in the freeze-drying buffer containing the chelating agent, exosome amount was increased (FIG. 1).

Therefore, it was demonstrated that the chelating agent can stabilize the exosomes in the freeze-drying of exosomes.

Example 2: Stabilization of Exosome with Sucrose

The influence of saccharide on the freeze-drying of exosomes was investigated.
1) Recovery of Exosome A culture supernatant of human colon carcinoma cell line SW480 cultured in the serum-free medium for three days was used as a sample. The culture supernatant was centrifuged at 2,000×g at 4° C. for 5 minutes, then filtered through the 0.22 μm filter (manufactured by Millipore Corp.), and then concentrated using Amicon Ultra-15 (manufactured by Millipore Corp.). The concentrate was centrifuged at 20,000×g at 4° C. for 15 minutes. Next, the supernatant was centrifuged at 100,000×g at 4° C. for 1 hour. The supernatant was discarded, and then PBS was added to resuspend the precipitate. Then, the resuspension was centrifuged at 100,000×g at 4° C. for 1 hour. The supernatant was discarded, and PBS was newly added to resuspend the precipitate in order to recover exosomes.
2) Freeze-Drying of Exosome Protein quantification was performed for the recovered exosomes with Qubit (trademark) Protein Assay Kit (manufactured by Thermo Fisher Scientific Inc.). Then, PBS was further added to each of the recovered exosomes to prepare solutions containing the same concentration of protein. Next, 1 volume of the recovered exosomes was mixed with 24 volumes of the freeze-drying buffer. After dispensation, the solution was freeze-dried with the above-mentioned freeze dryer with a program of −28° C. for 2 hours, −10° C. for 4 hours and subsequent 20° C., in order to obtain a freeze-dried product containing freeze-dried exosomes. As the freeze-drying buffer, PBS, EDTA/EGTA/PBS (final conc. 50 mM EDTA/50 mM EGTA), sucrose/PBS (final conc. 10 mg/mL sucrose), or EDTA/EGTA/sucrose/PBS (final conc. 50 mM EDTA/50 mM EGTA/10 mg/mL sucrose) was used.

Subsequently, the freeze-dried product was dissolved in milli-Q water (manufactured by Millipore Corp.).
3) Assessment of Stability of Exosome Based on Measurement of Amount of Exosome-Specific Antigen (CD9)

The amount of the dissolved freeze-dried exosomes was measured by ELISA system. Specifically, PBS (pH 7.4) containing anti-CD9 antibody prepared in the applicant was added to the 96-well ELISA plate (manufactured by NUNC Inc.), and incubated overnight at 4° C. Then, each well was washed three times with PBS-T, 200 μL of PBS containing 0.5 wt % Casein was added, and incubated for 2 hours at room temperature. After washing with PBS-T, 100 μL of the dissolved freeze-dried product diluted with PBS was added to each well and incubated for 1 hour at 37° C. Then, after washing with PBS-T, 100 μL of PBS containing biotinylated anti-CD9 antibody prepared in the applicant and streptavidin conjugated alkaline phosphatase (SA-ALP, manufactured by GeneTex Co.) was added to each well, and then incubated for 1 hour at 37° C. Then, after washing with PBS, 100 μL of Lumipulse substrate solution was added to be allowed to react for 5 minutes at 37° C., and then emission count was measured at a 477 nm wavelength. The count of the sample obtained without the freeze-drying is defined as 100%.

Figure 2:
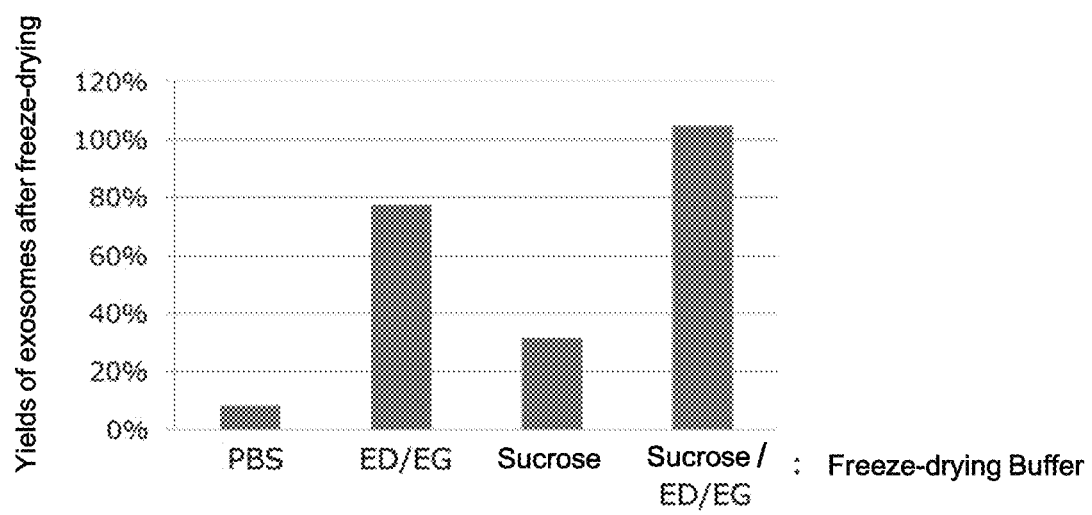
FIG. 2 is a graph of yields of exosomes obtained after freeze-drying under various buffer conditions in Example 2. Yields of exosomes obtained without freeze-drying are defined as 100%.
Figure 3A:
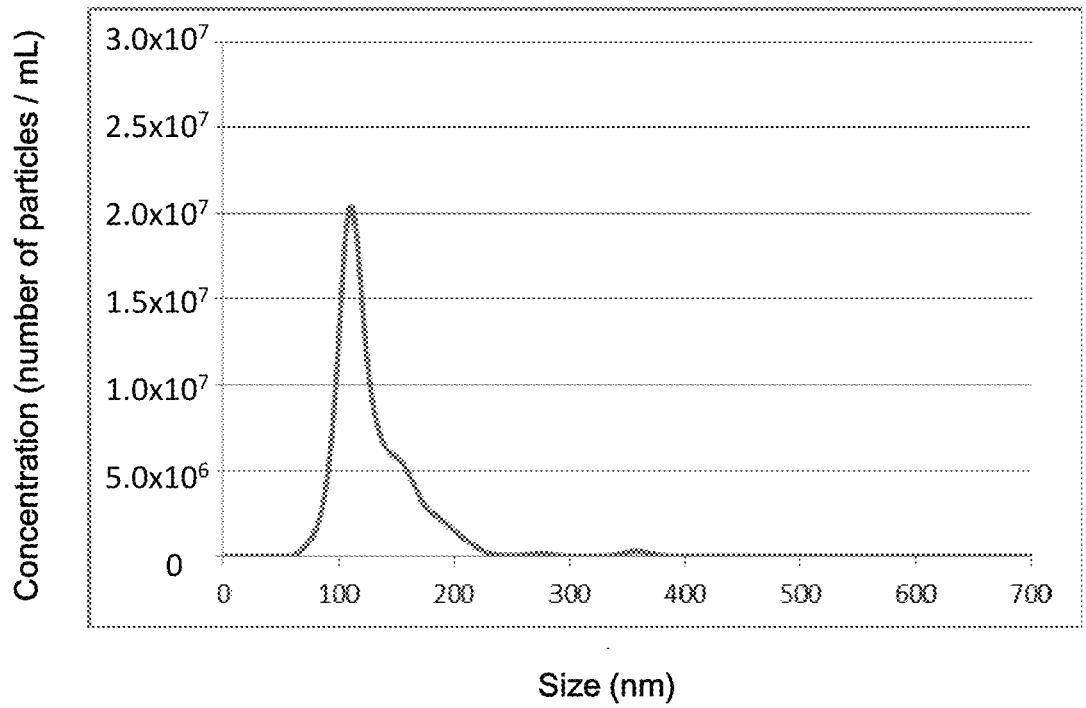
FIG. 3A is a graph of particle counts and a particle diameter distribution measured in a sample (Control) that is obtained before freeze-drying a culture supernatant of a human colon carcinoma cell line SW1116 in Example 3.
Figure 3B:
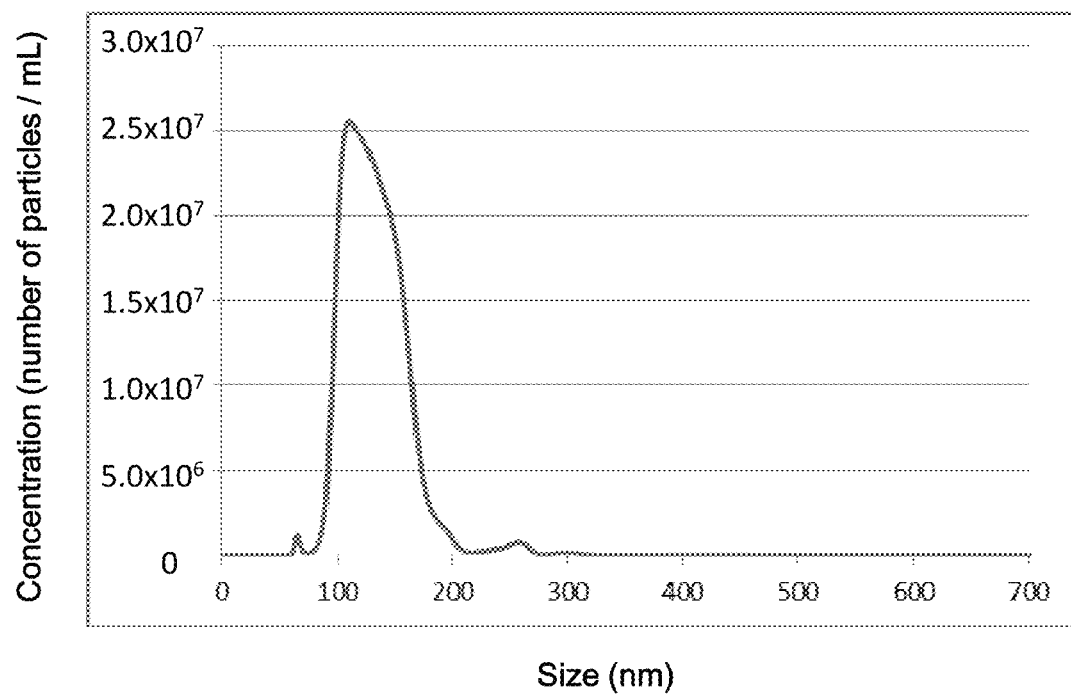
FIG. 3B is a graph of particle counts and a particle diameter distribution measured in a sample (ED/EG) that is obtained before freeze-drying the culture supernatant of the human colon carcinoma cell line SW1116 in Example 3.
Figure 3C:
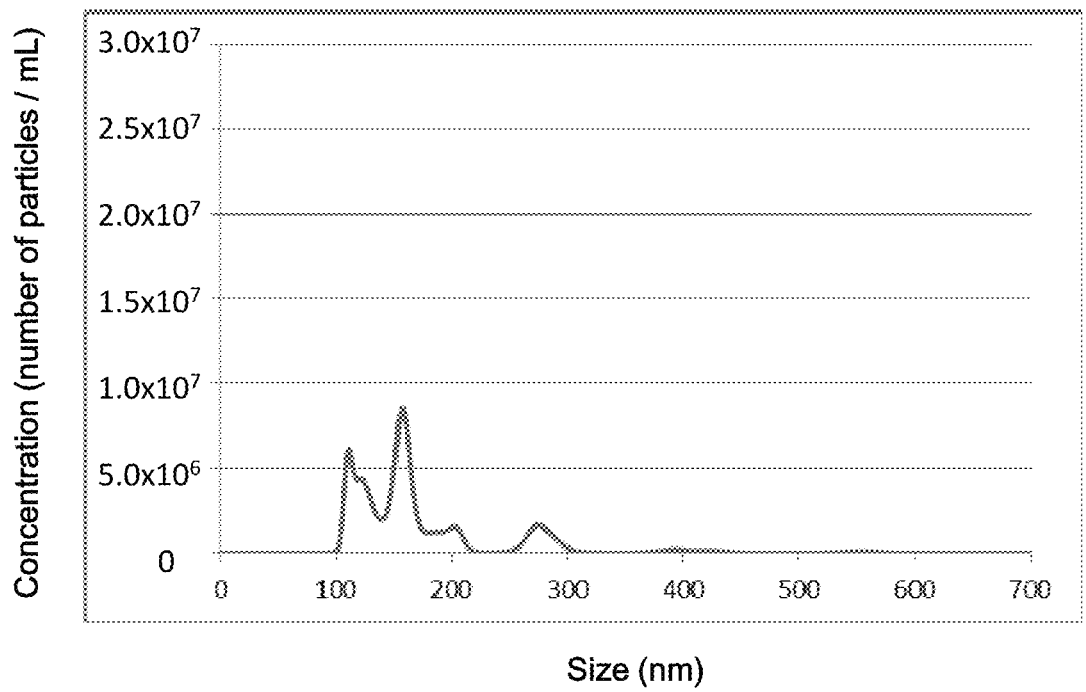
FIG. 3C is a graph of particle counts and a particle diameter distribution measured in a sample (Control) that is obtained after freeze-drying the culture supernatant of the human colon carcinoma cell line SW1116 in Example 3.
Figure 3D:
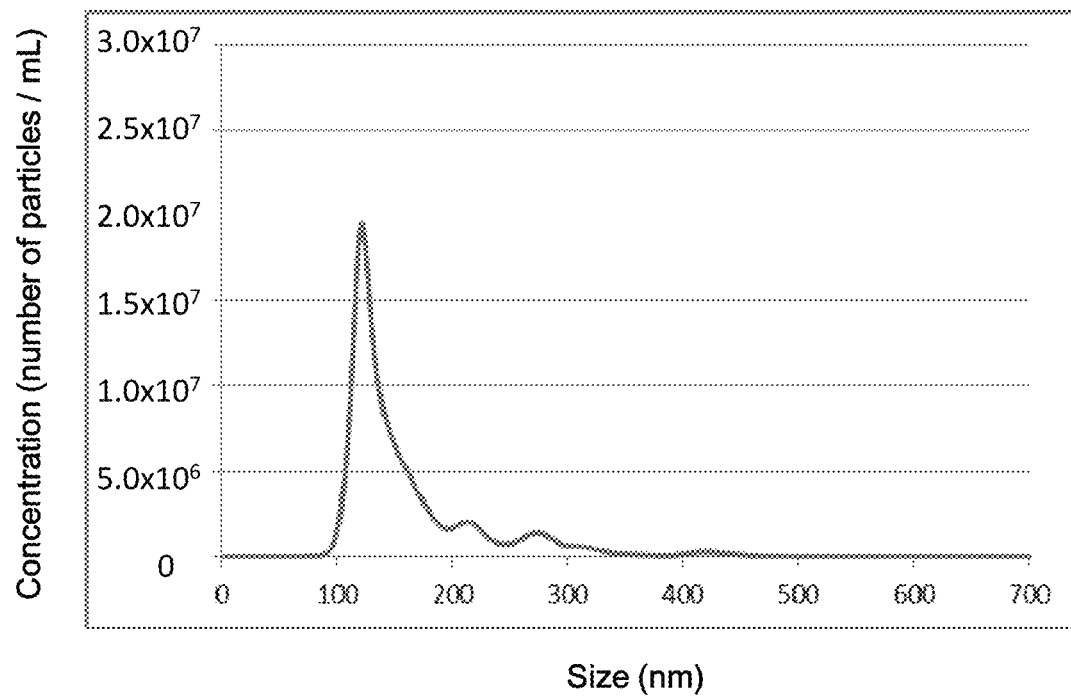
FIG. 3D is a graph of particle counts and a particle diameter distribution measured in a sample (ED/EG) that is obtained after freeze-drying the culture supernatant of the human colon carcinoma cell line SW1116 in Example 3.

As a result, in the freeze-drying buffer containing the sucrose, the exosome amount was increased (FIG. 2). Also, in the freeze-drying buffer containing the sucrose and the chelating agent, the exosome amount was further increased.

Therefore, it was demonstrated that the saccharide can stabilize the exosomes in the freeze-drying of exosomes. In addition, it was demonstrated that the stability of the exosomes with the saccharide can be enhanced in the presence of the chelating agent.

Example 3: Assessment of Stability of Freeze-Dried Exosome Based on Measurement of Particle Counts The stability was assessed on the basis of particle counts of the freeze-dried exosomes by measurement using NanoSight for a freeze-dried sample.
1) Recovery of Exosome A culture supernatant of human colon carcinoma cell line SW1116 cultured in the serum-free medium for three days was used as a sample. The culture supernatant was centrifuged at 2,000×g at 4° C. for 5 minutes, then filtered through the 0.22 μm filter (manufactured by Millipore Corp.), and then concentrated using Amicon Ultra-15 (manufactured by Millipore Corp.). The concentrate was centrifuged at 20,000×g at 4° C. for 15 minutes. Next, the supernatant was centrifuged at 100,000×g at 4° C. for 1 hour. The supernatant was discarded, and then PBS (Control) or 50 mM EDTA/50 mM EGTA/PBS (ED/EG) was added to resuspend the precipitate. Then, the resuspension was centrifuged at 100,000×g at 4° C. for one hour. The supernatant was discarded, and PBS or 50 mM EDTA/50 mM EGTA/PBS (ED/EG) was newly added to resuspend the precipitate in order to recover exosomes.
2) Freeze-Drying of Exosome Protein quantification was performed for the recovered exosomes with Qubit (trademark) Protein Assay Kit (manufactured by Thermo Fisher Scientific Inc.). Then, the recovery buffer was further added to each of the recovered exosomes to prepare solutions containing the same concentration of protein. Next, 1 volume of the recovered exosomes was mixed with 24 volumes of the freeze-drying buffer. After dispensation, the solution was freeze-dried with the abovementioned freeze dryer with a program of −28° C. for 2 hours, −10° C. for 4 hours and subsequent 20° C., in order to obtain a freeze-dried product containing freeze-dried exosomes. As the freeze-drying buffer, PBS and EDTA/EGTA/PBS (final conc. 50 mM EDTA/50 mM EGTA) (ED/EG) was used.

Subsequently, the freeze-dried product was dissolved in milli-Q water (manufactured by Millipore Corp.).
3) Assessment of Stability of Freeze-Dried Exosome The number and size distribution of the particles were measured by NanoSight LM10 (manufactured by Malvern Instruments) for the dissolved freeze-dried exosomes. The measurement was performed for 30 seconds and repeated three times. The analysis was carried out with a detection threshold of 15.

As a result, the number of particles with 100 to 200 nm diameter considered to be exosomes was increased in the freeze-drying buffer containing the chelating agent (Table 1 and FIGS. 3A to 3D).

Therefore, it was demonstrated that the chelating agent can stabilize the exosomes in the freeze-drying of exosomes also by the measurement of the number of particle.

TABLE 1

Number of particles corresponding to exosomes before and after freeze-drying

| Pa/mL | Control | ED/EG |
| --- | --- | --- |
| Before freeze-drying | $9.32 \times 10^8$ | $1.66 \times 10^9$ |
| After freeze-drying | $4.08 \times 10^8$ | $8.83 \times 10^8$ |
| vs. before freeze-drying | 44% | 53% |

Reference Example 1: Treatment of Exosomes with Various Chelating Agents

For chelating agents, disodium ethylenediaminetetraacetate (EDTA·2Na), glycoletherdiaminetetraacetic acid (EGTA), hydroxyethyl ethylenediaminetriacetic acid (HEDTA), hydroxyethyliminodiacetic acid (HIDA), nitrilotriacetic acid (NTA), oxalic acid dihydrate, ethylenediaminetetra (methylenephosphonic acid) (EDTMP) (EDTA·2Na, EGTA were from Dojindo Molecular Technologies, Inc., HEDTA, HIDA, NTA, EDTMP were from Tokyo Chemical Industry Co., Ltd., and oxalic acid dihydrate was from Wako Pure Chemical Industries, Ltd.) were used. The influences of each chelating agent on the precipitation amounts of exosomes were investigated.

300 µL of a serum specimen or a plasma specimen was diluted with 600 µL of PBS or each chelating agent-added PBS. The concentrations of each chelating agent to be used were 1, 10, and 50 mM at final concentrations (provided, 1, 10, and 30 mM only for EDTMP). Then, the solutions were left to stand at room temperature for 30 minutes, and then centrifuged at 20,000×g at 4° C. for 15 minutes. The resulting supernatant was transferred to a new tube, and magnetic beads (Protein G Dynabeads) immobilized with 2 µg of the monoclonal antibody recognizing CD9 prepared in the applicant were added thereto. After reacting at 4° C. overnight, the magnetic beads were washed three times with PBS, and the samples were eluted with the sample buffer (containing SDS) from the magnetic beads to use as samples for western blotting. These samples were analyzed by western blotting using the biotinylated anti-CD9 antibody.

Figure 4A:
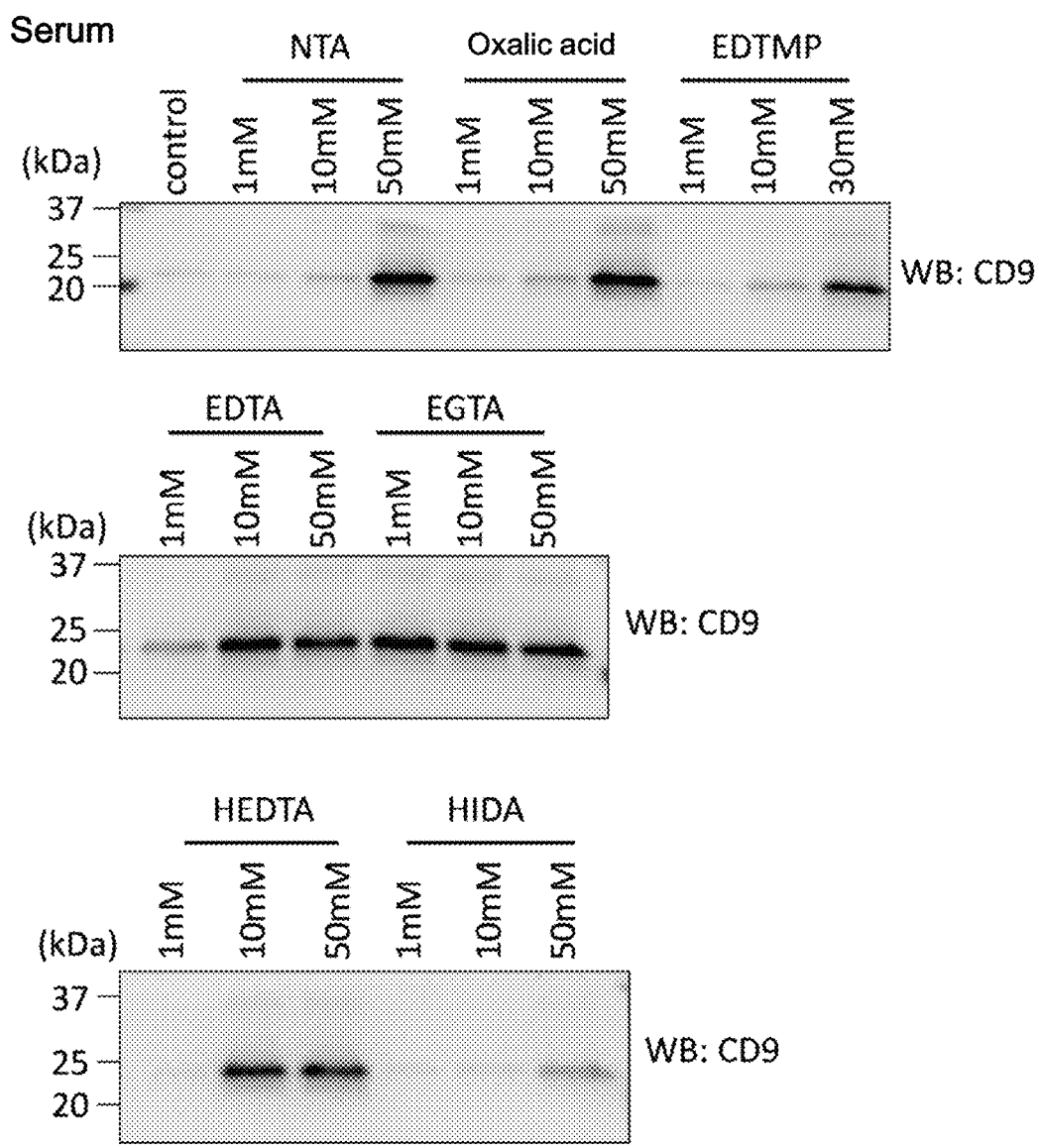
FIG. 4A is a diagram depicting results of western blotting with a biotinylated anti-CD9 antibody of samples obtained from an immunoprecipitation method of a serum specimen that is mixed with each of various chelating agents at different concentrations in Reference Example 1.
Figure 4B:
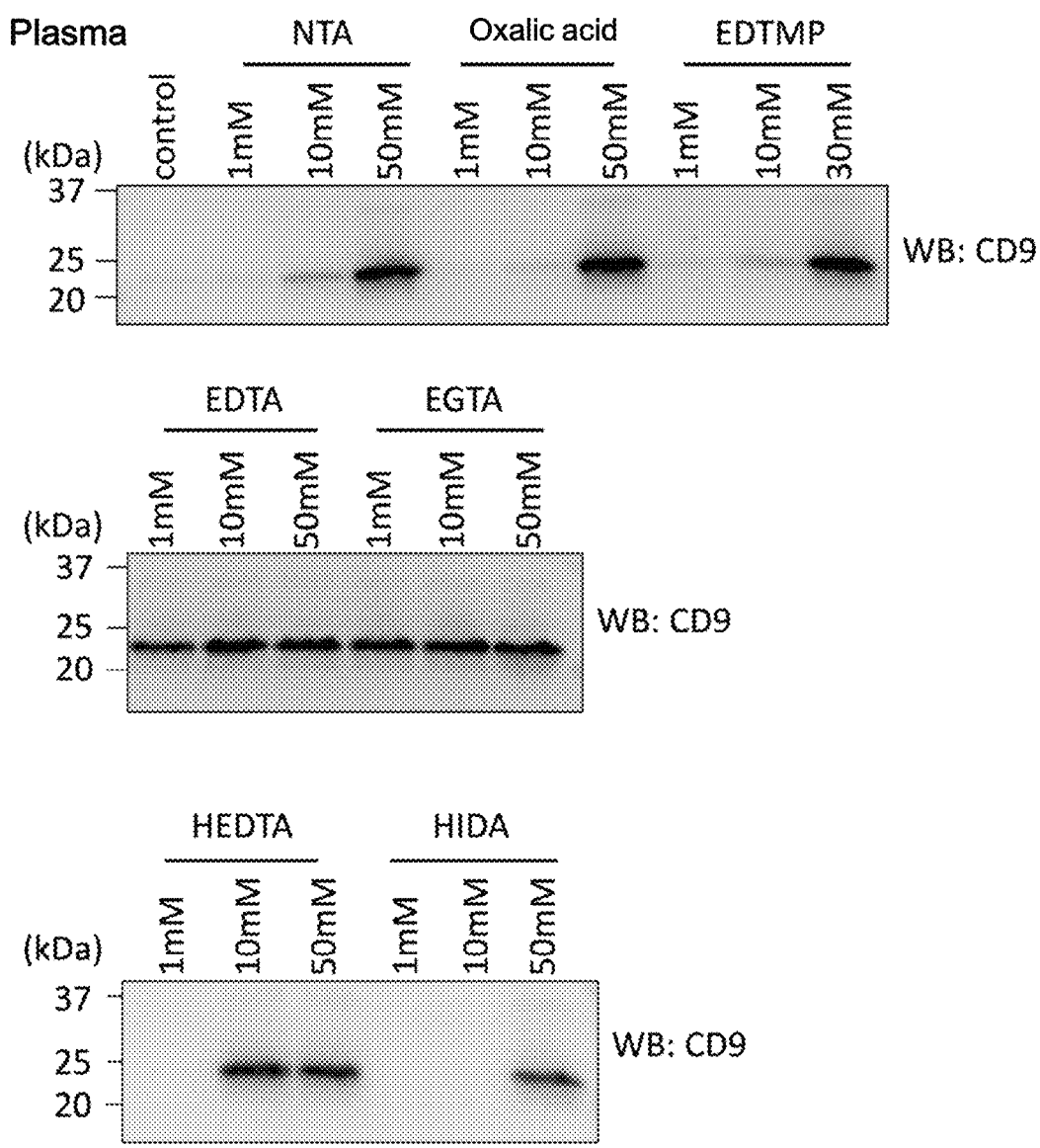
FIG. 4B is a diagram depicting results of western blotting with the biotinylated anti-CD9 antibody of samples obtained from the immunoprecipitation method of a plasma specimen that is mixed with each of various chelating agents at different concentrations in Reference Example 1.

As a result, all of the chelating agents used showed recovery of exosomes by immunoprecipitation both in the serum specimens (FIG. 4A) and the plasma specimens (FIG. 4B). In addition, as the concentration of the chelating agent increased, the amount of the immunoprecipitated exosomes increased. In particular, the immunoprecipitation amounts of exosomes drastically increased under the conditions of 30 mM EDTMP, 50 mM EDTA, EGTA, HEDTA, NTA and oxalic acid (FIGS. 4A and 4B).

Example 4: Stabilization of Exosome with Various Saccharides

The influence of various saccharides on the freeze-drying of exosomes was investigated.
1) Recovery of Exosome
The culture supernatant of the human non-small cell lung carcinoma cell line H1299 cultured in the serum-free medium for three days was used as a sample. The exosomes were recovered by the recovery method in Example 2.

2) Freeze-Drying of Exosome
Protein quantification was performed for the recovered exosomes with Qubit (trademark) Protein Assay Kit (manufactured by Thermo Fisher Scientific Inc.). Then, PBS was further added to each of the recovered exosomes to prepare solutions containing the same concentration of protein. Next, 1 volume of the recovered exosomes was mixed with 9 volumes of the freeze-drying buffer. After dispensation, the solution was freeze-dried with a freeze dryer (manufactured by Genevac Ltd.) in order to obtain a freeze-dried product containing freeze-dried exosomes. As the freeze-drying buffer, PBS and PBS solutions, each of that contains one of lactose, fructose, methyl β-cyclodextrin (MβCD), hydroxypropyl β-cyclodextrin (HpβCD), γ-cyclodextrin (γCD), glucose, lactitol, sorbitol, xylitol, sucrose, trehalose, mannitol and xylose in a final concentration of 2.0 mg/mL, 10 mg/mL and 50 mg/mL, were used.

Subsequently, the freeze-dried product was dissolved in milli-Q water (manufactured by Millipore Corp.).
3) Assessment of Stability of Exosome Based on Measurement of Amount of Exosome-Specific Antigen (CD9)
The amount of the dissolved freeze-dried exosomes was measured by ELISA system. Specifically, PBS (pH 7.4) containing anti-CD9 antibody prepared in the applicant was added to the 96-well ELISA plate (manufactured by NUNC Inc.), and incubated overnight at 4° C. Then, each well was washed three times with PBS-T, 200 µL of PBS containing 0.5 wt % BSA was added, and incubated for 2 hours at room temperature. After washing with PBS-T, 100 µL of the dissolved freeze-dried product was added to each well and incubated for 1 hour at 37° C. Then, after washing with PBS-T, 100 µL of PBS containing biotinylated anti-CD9 antibody prepared in the applicant was added to each well, and then incubated for 1 hour at 37° C. Then, after washing with PBS-T, 100 µL of PBS containing streptavidin-conjugated alkaline phosphatase (SA-ALP, manufactured by GeneTex, Inc.) was added to each well, and then incubated for 1 hour at 37° C. Then, after washing with PBS-T, 100 µL of Lumipulse substrate solution was added to be allowed to react for 5 minutes at 37° C., and then emission count was measured at a 480 nm wavelength. The count of the sample obtained without the freeze-drying is defined as 100%.

Figure 5A:
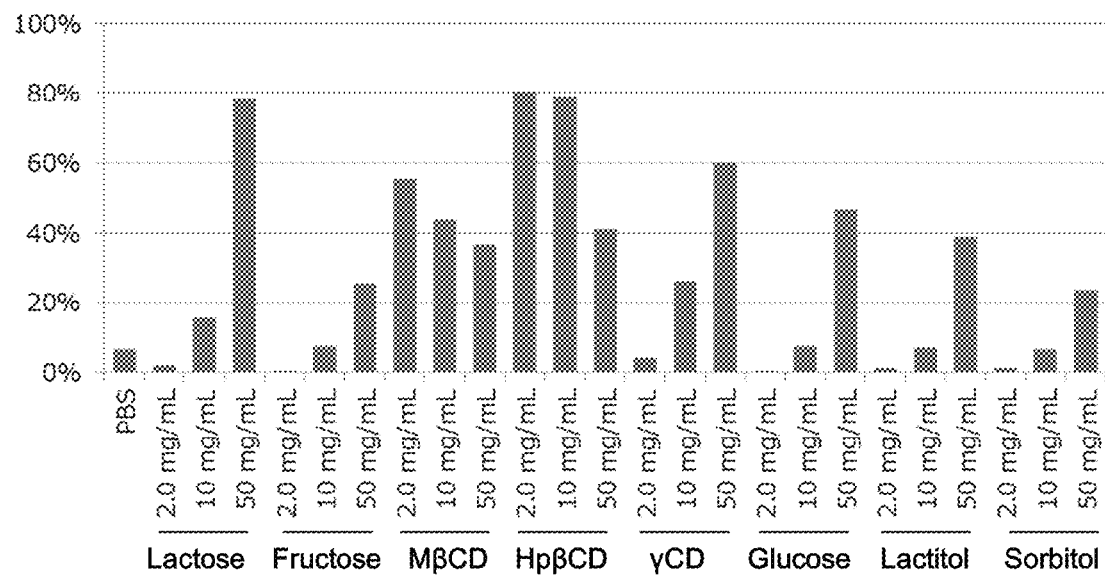
FIG. 5A is a graph (continued on FIG. 5B) of yields of exosomes obtained after freeze-drying under various buffer conditions in Example 4. Yields of exosomes obtained without freeze-drying are defined as 100%.
Figure 5B:
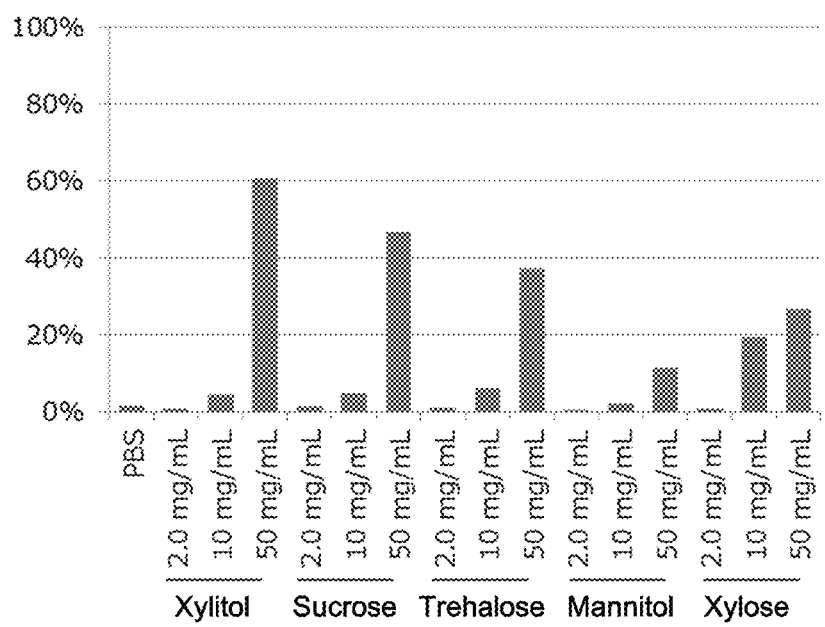
FIG. 5B is a graph of yields of exosomes obtained after freeze-drying under various buffer conditions in Example 4. Yields of exosomes obtained without freeze-drying are defined as 100%.

As a result, in the freeze-drying buffers each containing the saccharide, the exosome amount was increased (FIGS. 5A and 5B). In particular, most of the investigated saccharides increased the exosome amount in the freeze-drying buffers each containing 10 mg/mL or 50 mg/mL of the saccharide.

Therefore, it was demonstrated that each of the saccharides can stabilize the exosomes in the freeze-drying of exosomes, and in particular, exhibit a high stabilization effect in the case of 10 to 50 mg/mL of the saccharide.

Example 5: Stabilization of Exosome in Combination Use of Various Saccharides and Chelating Agent The influence of combination use of various saccharides and chelating agent on the freeze-drying of exosomes was investigated.
1) Exosome Recovery, Freeze-Drying of Exosome and Assessment of Stability of Exosome Based on the Measurement of Amount of Exosome-Specific Antigen (CD9)
The exosome recovery, the freeze-drying of exosome and assessment of stability of exosomes were carried out by the method described in Example 4 other than the freeze-dying buffer.

PBS, EDTA/EGTA/PBS (final conc. 50 mM EDTA/50 mM EGTA) (ED/EG), or either one thereof that contains lactose, γ-cyclodextrin (γCD), glucose or lactitol in a final concentration of 10 mg/mL, was used as the freeze-drying buffer.

Figure 6:
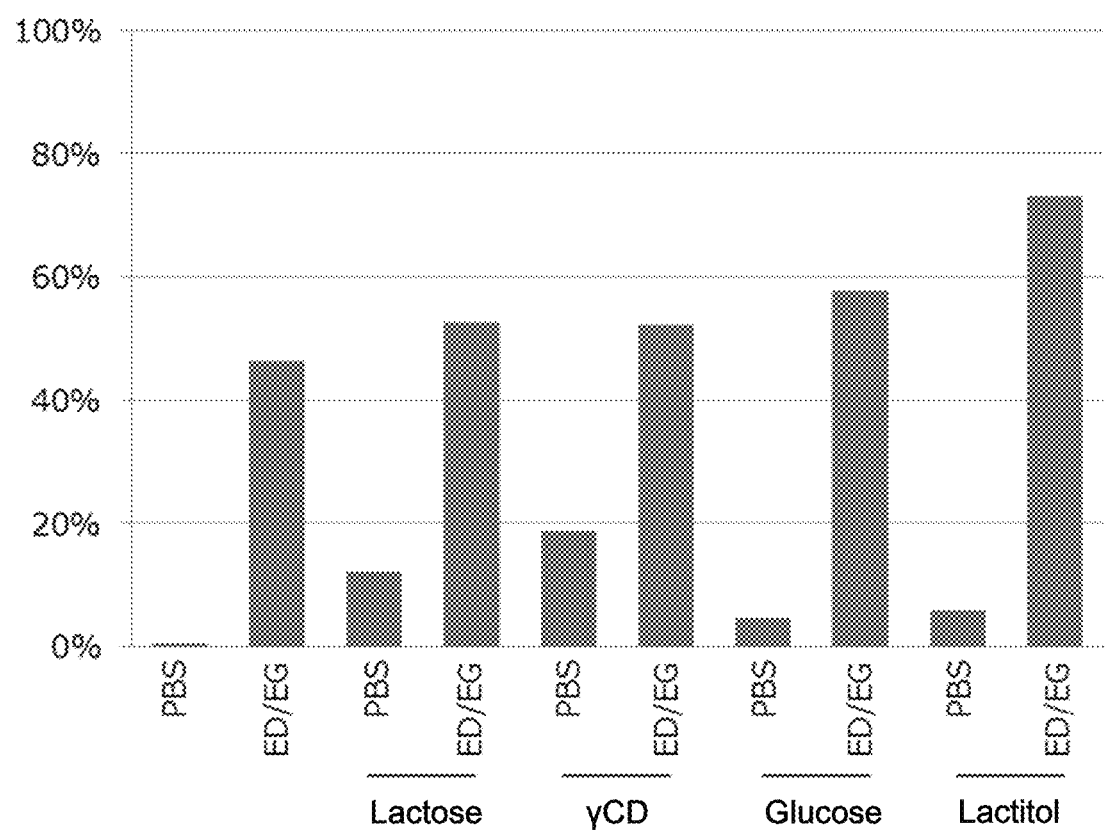
FIG. 6 is a graph of yields of exosomes obtained after freeze-drying under various buffer conditions in Example 5. Yields of exosomes obtained without freeze-drying are defined as 100%.

As a result, in the freeze-drying buffers containing the saccharide and the chelating agent, the exosome amount was increased (FIG. 6).

Therefore, it was demonstrated that the stabilization of exosomes by the saccharide can be enhanced in the presence of the chelating agent.

Example 6: Stabilization of Exosome Derived From Serum

The influence of various saccharides, the chelating agent or a combination use thereof on the freeze-drying of exosomes derived from serum was investigated.

1) Recovery of Exosome

Human serum was used as a sample. The serum was centrifuged at 2,000×g at 4° C. for 5 minutes, and then centrifuged at 20,000×g at 4° C. for 15 minutes. Next, the supernatant was centrifuged at 100,000×g at 4° C. for 3 hours. The supernatant was discarded, and then PBS was added to resuspend the precipitate. Then, the resuspension was centrifuged at 100,000×g at 4° C. for 1 hour. The supernatant was discarded, and PBS was newly added to resuspend the precipitate in order to recover exosomes.

2) Freeze-Drying of Exosome and Assessment of Stability of Exosome Based on Measurement of Amount of Exosome-Specific Antigen (CD9)

The freeze-drying of exosomes and assessment of stability of exosomes were carried out by the method described in Example 4 other than the freeze-dying buffer.

PBS, EDTA/EGTA/PBS (final conc. 50 mM EDTA/50 mM EGTA) (ED/EG), or either one thereof that contains lactose, glucose or lactitol in a final concentration of 10 mg/mL or 50 mg/mL, was used as the freeze-drying buffer.

Figure 7:
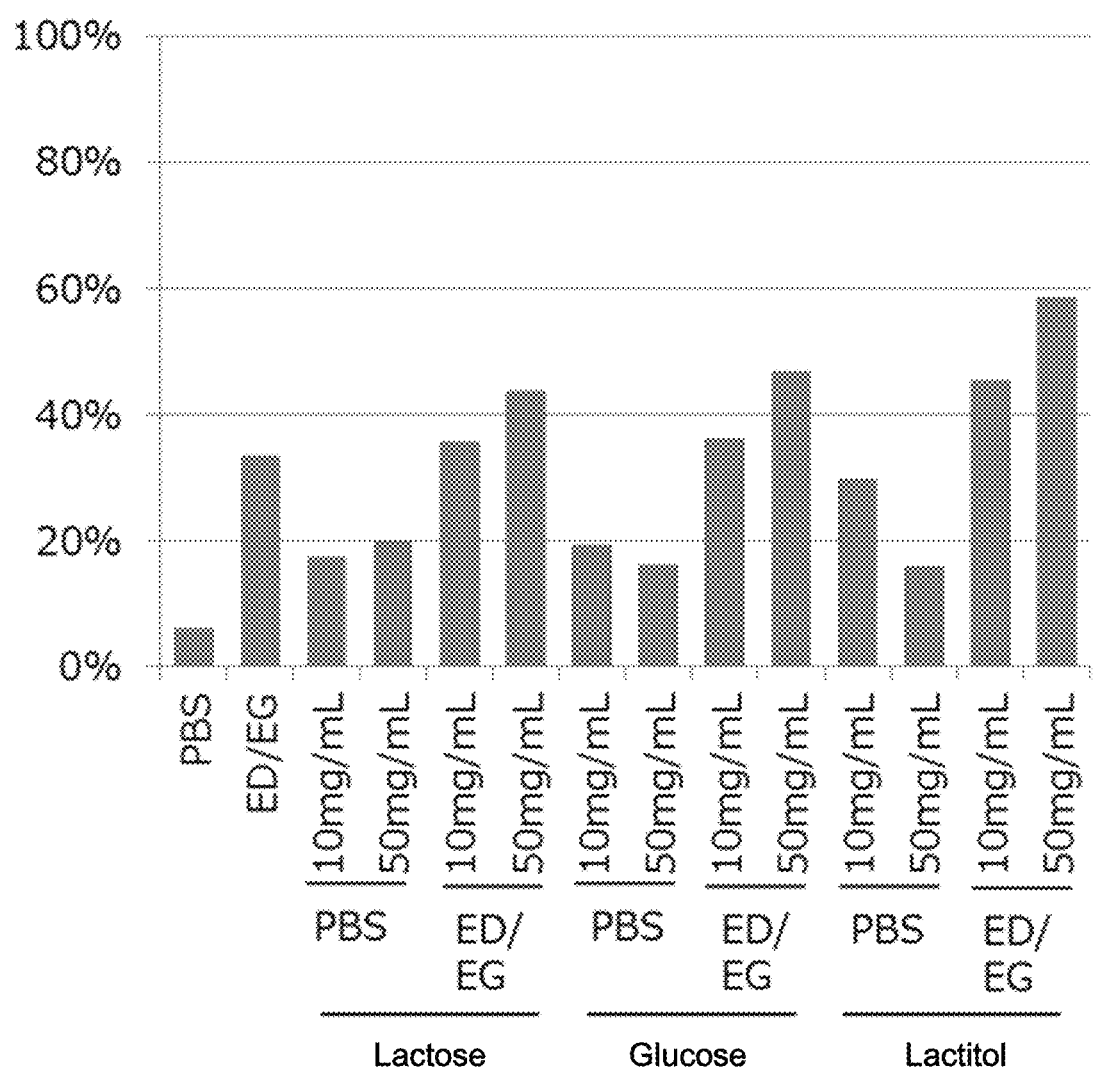
FIG. 7 is a graph of yields of exosomes obtained after freeze-drying a human serum sample under various buffer conditions in Example 6. Yields of exosomes obtained without freeze-drying are defined as 100%.

As a result, in the freeze-drying buffers containing the saccharides or the chelating agent, the exosome amount was increased (FIG. 7). The exosome amount was further increased in the case of using the freeze-drying buffers containing both of the saccharide and the chelating agent.

Therefore, it was demonstrated that the stabilization effect of exosomes by the saccharide and the chelating agent was proven to be enhanced also for the exosomes derived from the serum.

Example 7: Stabilization of Exosomes with Carboxymethyl Cellulose

The influence of carboxymethyl cellulose (CMC) on the freeze-drying of exosomes was investigated.

1) Recovery of Exosome

The culture supernatant of the human non-small cell lung carcinoma cell line H1299 cultured in the serum-free medium for three days was used as a sample. The culture supernatant was centrifuged at 2,000×g at 4° C. for 5 minutes, then filtered through the 0.22 μm filter (manufactured by Millipore Corp.), and then concentrated using Amicon Ultra-15 (manufactured by Millipore Corp.). The concentrate was centrifuged at 100,000×g at 4° C. for 3 hours. Next, the supernatant was discarded, and then PBS was added to resuspend the precipitate. Then, the resuspension was centrifuged at 100,000×g at 4° C. for 1 hour. The supernatant was discarded, and PBS was newly added in order to recover exosomes.

2) Freeze-Drying of Exosome

Protein quantification was performed for the recovered exosomes with Qubit (trademark) Protein Assay Kit (manufactured by Thermo Fisher Scientific Inc.), and concentration was adjusted. Next, 1 volume of the recovered exosomes was mixed with an equivalent volume of the freeze-drying buffer, frozen at −20° C. for 3 hours, and then dried with a centrifugal evaporator (manufactured by Scrum Inc.). Then, the freeze-dried product was dissolved in milli-Q water (manufactured by Millipore Corp.) and diluted with PBS. PBS and CMC/PBS (final conc. 0.2 wt % or 1 wt % CMC) were used as the freeze-drying buffers.

3) Assessment of Stability of Exosome Based on Measurement of Amount of Exosome-Specific Antigen (CD9)

The amount of the dissolved freeze-dried exosomes was evaluated by ELISA system in which the anti-CD9 antibody prepared in the applicant was used in a solid phase and the biotinylated anti-CD9 antibody prepared in the applicant and SA-ALP (manufactured by GeneTex, Inc.) were used for detection. In the evaluation, the count of the sample obtained without the freeze-drying was defined as 100%.

Figure 8:
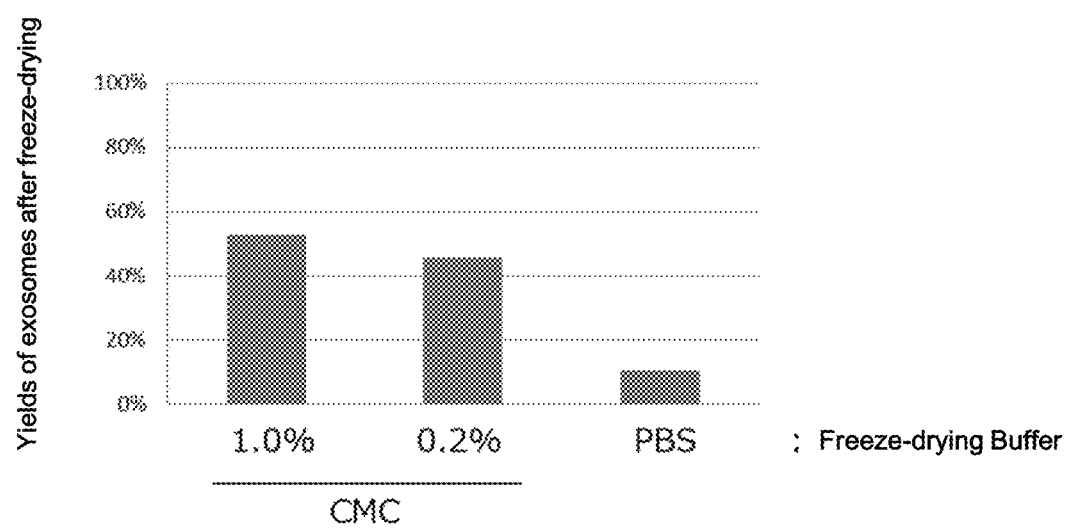
FIG. 8 is a graph of yields of exosomes obtained after freeze-drying under various buffer conditions in Example 7. Yields of exosomes obtained without freeze-drying are defined as 100%.

As a result, under the condition containing 0.2 wt % CMC or 1 wt % CMC in the freeze-drying, residual amount of exosomes is increased (FIG. 8).

Therefore, it was demonstrated that CMC can stabilize the exosomes in the freeze-drying of exosomes.

The invention claimed is:

1. A method of stabilizing an extracellular vesicle, the method comprising:
   mixing the extracellular vesicle-containing sample with a first chelating agent, to obtain a first mixture;
   separating the first mixture into (i) a liquid portion comprising the first chelating agent and (ii) a precipitation portion comprising the extracellular vesicles;
   removing the liquid portion;
   recovering the precipitation portion;
   mixing the precipitation portion with a second chelating agent in a first solution to obtain a second mixture;
   freeze-drying the second mixture to obtain a freeze-dried extracellular vesicle; and
   dissolving the freeze-dried extracellular vesicle in a second solution.

2. The method of claim 1, wherein a concentration of the first chelating agent in the mixing is from 20 to 200 mM.

3. The method of claim 1, wherein a concentration of the first chelating agent in the mixing is from 40 to 200 mM.

4. The method of claim 1, wherein a concentration of the first chelating agent in the mixing is from 50 to 200 mM.

5. The method of claim 1, wherein the mixing the precipitation portion with a second chelating agent in a first solution to obtain a second mixture is carried out by mixing the precipitation portion with the chelating agent in the presence of a saccharide.

6. The method of claim 5, wherein a concentration of the saccharide in the mixing is from 2.5 to 100 mg/mL.

7. The method according to claim 1, wherein the extracellular vesicle is an exosome.

8. The method of claim 1, wherein the extracellular vesicle-containing sample is a body fluid or a culture supernatant.

9. The method of claim 1, wherein the extracellular vesicle-containing sample is a blood sample.

10. The method of claim 5, wherein a concentration of the second chelating agent is from 1 to 200 mM per 10 mg/mL of the saccharide.

* * * * *